United States Patent
Cavallaro et al.

(10) Patent No.: US 10,060,868 B2
(45) Date of Patent: Aug. 28, 2018

(54) CALCULATING AN EFFECTIVE HEAT TRANSFER COEFFICIENT OF A DEVICE

(71) Applicant: Motorola Mobility LLC, Chicago, IL (US)

(72) Inventors: Alberto R Cavallaro, Northbrook, IL (US); Maninder Sehmbey, Hoffman Estates, IL (US)

(73) Assignee: Motorola Mobility LLC, Chicago, IL (US)

( * ) Notice: Subject to any disclaimer, the term of this patent is extended or adjusted under 35 U.S.C. 154(b) by 360 days.

(21) Appl. No.: 14/995,230

(22) Filed: Jan. 14, 2016

(65) Prior Publication Data

US 2017/0205365 A1    Jul. 20, 2017

(51) Int. Cl.

| | | |
|---|---|---|
| G01K 17/00 | (2006.01) |
| G01N 25/20 | (2006.01) |
| G01K 7/42 | (2006.01) |
| G01K 7/16 | (2006.01) |
| G05D 23/27 | (2006.01) |
| G06F 1/20 | (2006.01) |
| G06F 9/30 | (2018.01) |
| G06F 9/48 | (2006.01) |

(52) U.S. Cl.
CPC .............. *G01N 25/20* (2013.01); *G01K 7/16* (2013.01); *G01K 7/425* (2013.01); *G01K 7/427* (2013.01); *G05D 23/27* (2013.01); *G06F 1/206* (2013.01); *G06F 9/30083* (2013.01); *G06F 9/4893* (2013.01)

(58) Field of Classification Search
CPC ...... G01N 25/20; G06F 1/206; G06F 9/30083; G06F 9/4893; G05D 23/27; G01K 7/16; G01K 7/425; G01K 7/427
See application file for complete search history.

(56) References Cited

U.S. PATENT DOCUMENTS

| | | | | |
|---|---|---|---|---|
| 8,452,463 | B2* | 5/2013 | Cox | G06F 1/206 |
| | | | | 700/299 |
| 9,500,538 | B2* | 11/2016 | Maleki | H01M 10/486 |
| 9,518,873 | B2* | 12/2016 | Bellamkonda | G01K 7/42 |

(Continued)

OTHER PUBLICATIONS

Sensirion, "Humidity and Temperature Sensors Widen Potential for Wearable Devices", 2016, 4 pages.

(Continued)

*Primary Examiner* — Toan Le
(74) *Attorney, Agent, or Firm* — Yudell Isidore PLLC (57) ABSTRACT

A method, a system, and computer program product for calculating an effective heat transfer coefficient of a device. The method includes measuring: an internal temperature of the device, a first temperature at a first location along a first resistive path of a parallel resistive network and a second temperature at a second location along a second resistive path of the parallel resistive network. An ambient temperature of the environment and an effective heat transfer coefficient of the device is then calculated based on the internal temperature, the first temperature, the second temperature, and resistive properties of the parallel resistive network. The ambient temperature and the effective heat transfer coefficient are provided to a thermal management component.

19 Claims, 5 Drawing Sheets

(56) References Cited

U.S. PATENT DOCUMENTS

| | | | | |
|---|---|---|---|---|
| 2006/0013218 A1* | 1/2006 | Shore | ............... | H04L 29/06027 370/389 |
| 2007/0152674 A1* | 7/2007 | Hubbell | ................. | H01L 23/34 324/509 |
| 2013/0319640 A1* | 12/2013 | Cavallaro | ................ | F28F 7/00 165/121 |
| 2016/0299186 A1* | 10/2016 | Fan | ........................ | G01R 31/07 |
| 2017/0102676 A1* | 4/2017 | Park | ....................... | G05B 15/02 |
| 2017/0164220 A1* | 6/2017 | Roessel | ............ | H04W 52/0261 |

OTHER PUBLICATIONS

Sensirion, "Humidity and Temperature Sensor IC", Datasheet SHT3x-ARP, www.sensirion.com, Version 2, Jan. 2016, 13 pages.

* cited by examiner

CALCULATING AN EFFECTIVE HEAT TRANSFER COEFFICIENT OF A DEVICE

BACKGROUND

1. Technical Field

The present disclosure generally relates to electronic devices and in particular to an improved method for calculating an ambient temperature of an environment and an effective heat transfer coefficient of an electronic device.

2. Description of the Related Art

Due to numerous constraints, including size constraints, many electronic devices, such as a mobile device, are deliberately designed without active cooling solutions. Instead, these types of electronic devices rely on passive cooling by the device and continual monitoring of internal temperatures at key locations throughout the device. These key locations can include at the processor core, the memory, and/or various other locations throughout a printed circuit board. Solutions currently exist to maintain an internal temperature of a device below a threshold in order to protect the device from harmful conditions, such as a processor overheating. For example, an operating frequency of a processor may be throttled down when the processor's temperature reaches a threshold. However, these solutions regulate the operation of a device based entirely on the device's internal temperature and a pre-established acceptable internal temperature range and do not account for environmental conditions of the device. Additionally, current solutions are unable to measure an ambient temperature of an environment by a same device that is generating heat to the environment, and instead rely on receiving ambient temperature data from a secondary device, such as a remote computer or infrared thermometer.

BRIEF DESCRIPTION OF THE DRAWINGS

The description of the illustrative embodiments is to be read in conjunction with the accompanying drawings, wherein.

DETAILED DESCRIPTION

The illustrative embodiments provide a method, a system, and a computer program product for calculating an ambient temperature and an effective heat transfer coefficient of an electronic device. The method includes measuring an internal temperature at a particular location in the device. The method further includes, measuring a first temperature at a first location along a first resistive path of a parallel resistive network and measuring a second temperature at a second location along a second resistive path of the parallel resistive network. Based on the internal temperature, the first temperature, the second temperature, and pre-established resistive properties of the first and second resistive paths, an ambient temperature of the device is calculated independent of any heat generated by the device to the environment. The method further includes, calculating an effective heat transfer coefficient of the device that represents a rate at which heat generated by the device can be dissipated to the ambient environment in proportion to the temperature difference between the device and the calculated ambient temperature. The ambient temperature and the effective heat transfer coefficient are then provided to a thermal management component of the device.

The above contains simplifications, generalizations and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and the remaining detailed written description. The above as well as additional objectives, features, and advantages of the present disclosure will become apparent in the following description.

In the following detailed description, specific example embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various aspects are described which may be aspects for some embodiments but not other embodiments.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Moreover, the use of the terms first, second, etc. do not denote any order or importance, but rather the terms first, second, etc. are used to distinguish one element from another.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be provided its broadest interpretation given the context in which that term is utilized.

Those of ordinary skill in the art will appreciate that the hardware components and basic configuration depicted in the following figures may vary. For example, the illustrative components within device 100 are not intended to be exhaustive, but rather are representative to highlight components that are utilized to implement the present disclosure. For example, other devices/components may be used in addition to, or in place of, the hardware depicted. The depicted example is not meant to imply architectural or other limitations with respect to the presently described embodiments and/or the general disclosure.

Within the descriptions of the different views of the figures, the use of the same reference numerals and/or symbols in different drawings indicates similar or identical items, and similar elements can be provided similar names and reference numerals throughout the figure(s). The specific identifiers/names and reference numerals assigned to the elements are provided solely to aid in the description and are not meant to imply any limitations (structural or functional or otherwise) on the described embodiments.

Figure 1:
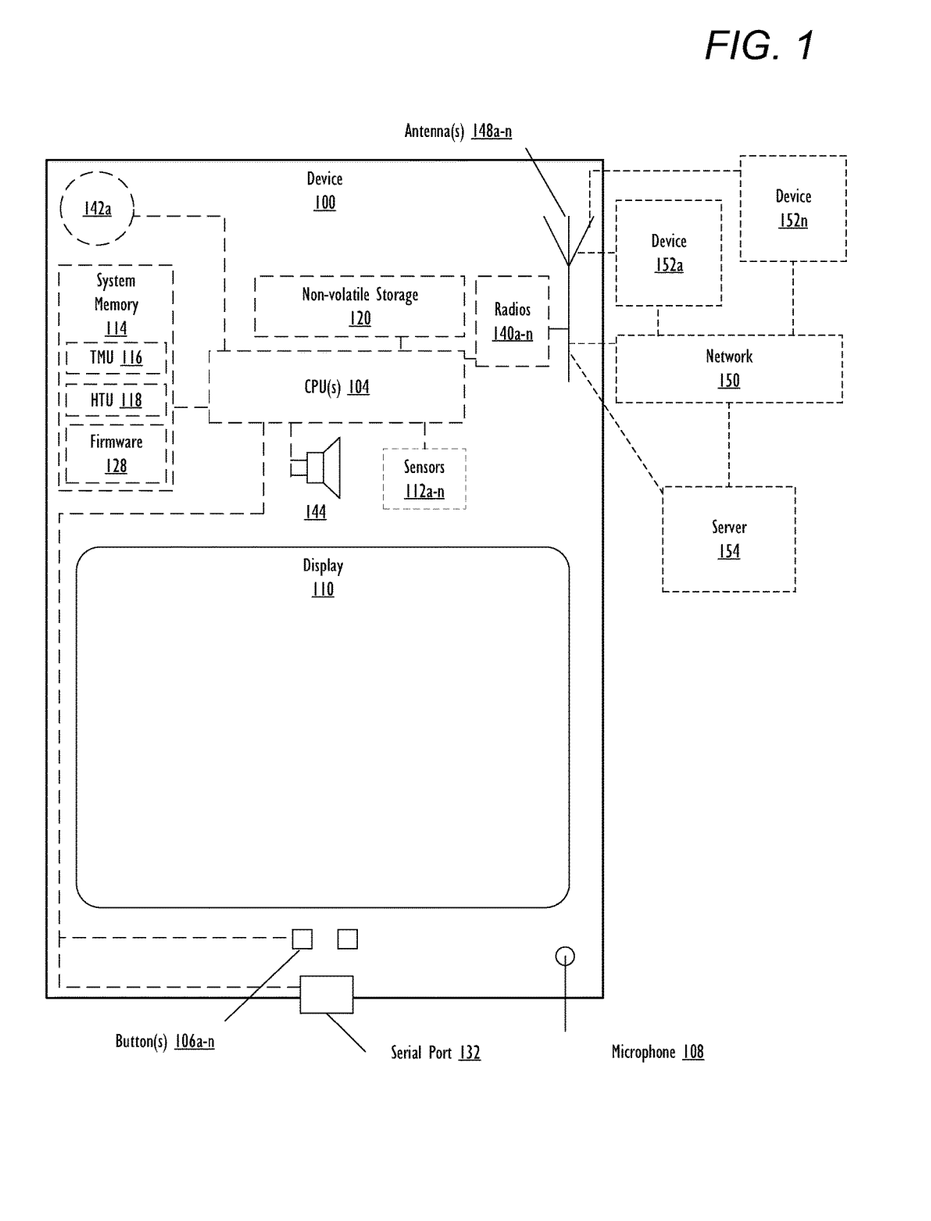
FIG. 1 provides a block diagram representation of a device within which certain aspects of the disclosure can be practiced, in accordance with one or more embodiments.

With reference now to the figures, and beginning with FIG. 1, there is depicted a block diagram representation of an example device 100, within which one or more of the described features of the various embodiments of the disclosure can be implemented. In one embodiment, device 100 can be any portable electronic device such as a notebook computer, fitness monitoring device, mobile phone, watch, smart watch, camera, video recorder, or tablet. In another embodiment, device 100 may be a generic data processing system.

Device 100 includes at least one central processing unit (CPU) or processor 104. CPU 104 is coupled to system memory 114 and/or non-volatile storage 120, within which firmware 128, thermal management utility (TMU) 116, and heat transfer utility (HTU) 118 can be stored for execution on CPU 104. According to one aspect, HTU 118 executes within device 100 to provide logic that performs the various methods and functions described herein. For simplicity, HTU 118 is illustrated and described as a stand-alone or separate software/firmware/logic component, which provides the specific functions and methods described below. However, in at least one embodiment, HTU 118 may be a component of, may be combined with, or may be incorporated within firmware 128 of device 100, or within an operating system (not pictured) and/or one or more applications (not pictured).

Device 100 also includes a TMU 116, which regulates the operation of CPU 104 and/or one or more input, output, or input/output components of device 100. In one embodiment, TMU 116 regulates the operation of components of device 100 based on at least one of a calculated or estimated temperature of an ambient environment of device 100 and a calculated effective heat transfer coefficient of device 100. TMU 116 receives both the calculated ambient temperature of an ambient environment and a calculated effective heat transfer coefficient of device 100 from CPU 104. In one embodiment, in response to receiving both of these calculated values, TMU 116 applies at least one modification to device 100, such as increasing or decreasing an operating frequency of CPU 104, adjusting a data input/output rate of wireless radios 140a-n, and adjusting a brightness of a backlight of display 110. TMU 116 is illustrated and described as a stand-alone software component. However, in at least one embodiment, the functionality of TMU 116 may be provided as a component of, may be combined with, or may be incorporated within firmware 128, HTU 118, or within an operating system (not pictured) and/or one or more applications (not pictured). In another embodiment, TMU 116 may execute on a dedicated processing unit separate from processor 104.

In one embodiment, TMU 116 may determine when a device 100 is not optimized for an ambient environment. TMU 116 may then independently determine and apply at least one modification to components of device 100 that corrects for at least one of (i) the effective heat transfer coefficient of device 100 and (ii) at least one environmental heat transfer condition in the ambient environment. In another embodiment, the at least one modification is determined by HTU 118, and TMU 116 receives instructions from CPU 104 that indicate at least one modification to apply to components of device 100.

As shown, device 100 comprises several input devices and output devices for enabling a user to interface with device 100. In the illustrated embodiment, device 100 includes a camera sensor 142, hardware buttons 106a-"n", microphone 108, and speaker 144. Microphone 108 may be used to receive spoken input/commands from a user, and/or ambient sound. Speaker 144 is used to output audio. Hardware buttons 106a-n are selectable buttons which are used to receive manual/tactile input from a user to control specific operations of device 100 and/or of applications executing thereon. In one embodiment, hardware buttons 106a-n may also include or be connected to one or more sensors (e.g. a fingerprint scanner) and/or be pressure sensitive. Hardware buttons 106a-n may also be directly associated with one or more functions of the GUI and/or functions of an OS, application, or hardware of device 100. In one embodiment, hardware buttons 106a-n may include a keyboard.

Device 100 also includes serial port 132 (e.g. a micro-USB (universal serial bus) port) which can be one of an input port, an output port, and an input/output port. Serial port 132 allows a direct physical connection to and communication of data with a second device. In one embodiment, serial port 132 may also connect to a power charger (not pictured) for charging a battery (not pictured) of device 100.

Device 100 also includes a display 110, which is capable of displaying a graphical user interface (GUI) of firmware and/or one or more applications executing on device 100. In one embodiment, display 110 is a touch screen that is also capable of receiving touch input from a user of device 100 interfacing with a displayed GUI. A GUI displayed by device 100 on display 110 may be rendered by CPU 104 and/or optionally by a graphical processing unit (GPU), if present.

Device 100 also includes one or more wireless radios 140*a-n* and one or more antenna(s) 148*a-n* that enable device 100 to wirelessly connect to, and transmit and receive data with, one or more other devices, such as devices 152*a-n* and server 154. As a wireless device, device 100 can transmit the data over a wireless network 150 (e.g., a Wi-Fi network, cellular network, Bluetooth network, or personal area network).

Device 100 also includes sensors 112*a-n*. As described in greater detail below, sensors 112*a-n* include at least a first thermal sensor at a first location (T1) along a first resistive path of a parallel resistive network, a second thermal sensor at a second location (T2) along a second resistive path of a parallel resistive network, and an internal thermal sensor at an internal location (T0) inside device 100. Thermal sensors may include any device for measuring a temperature of an environment, including analog temperature sensors, digital temperature sensors, and/or thermocouples. In another embodiment, sensors 112*a-n* may further include a surface temperature sensor for measuring a temperature of a surface of device 100. Sensors 112*a-n* can also include one or more of infrared (IR) sensors, ambient light sensors, proximity sensors, global positioning satellite (GPS) sensors, and sensors used for detecting motion, including, but not limited to, gyroscopic sensors, accelerometers, and magnetometers. In one embiment, one or more sensors of device 100 may be incorporated within another component of device 100, such as CPU 104.

Figure 2:
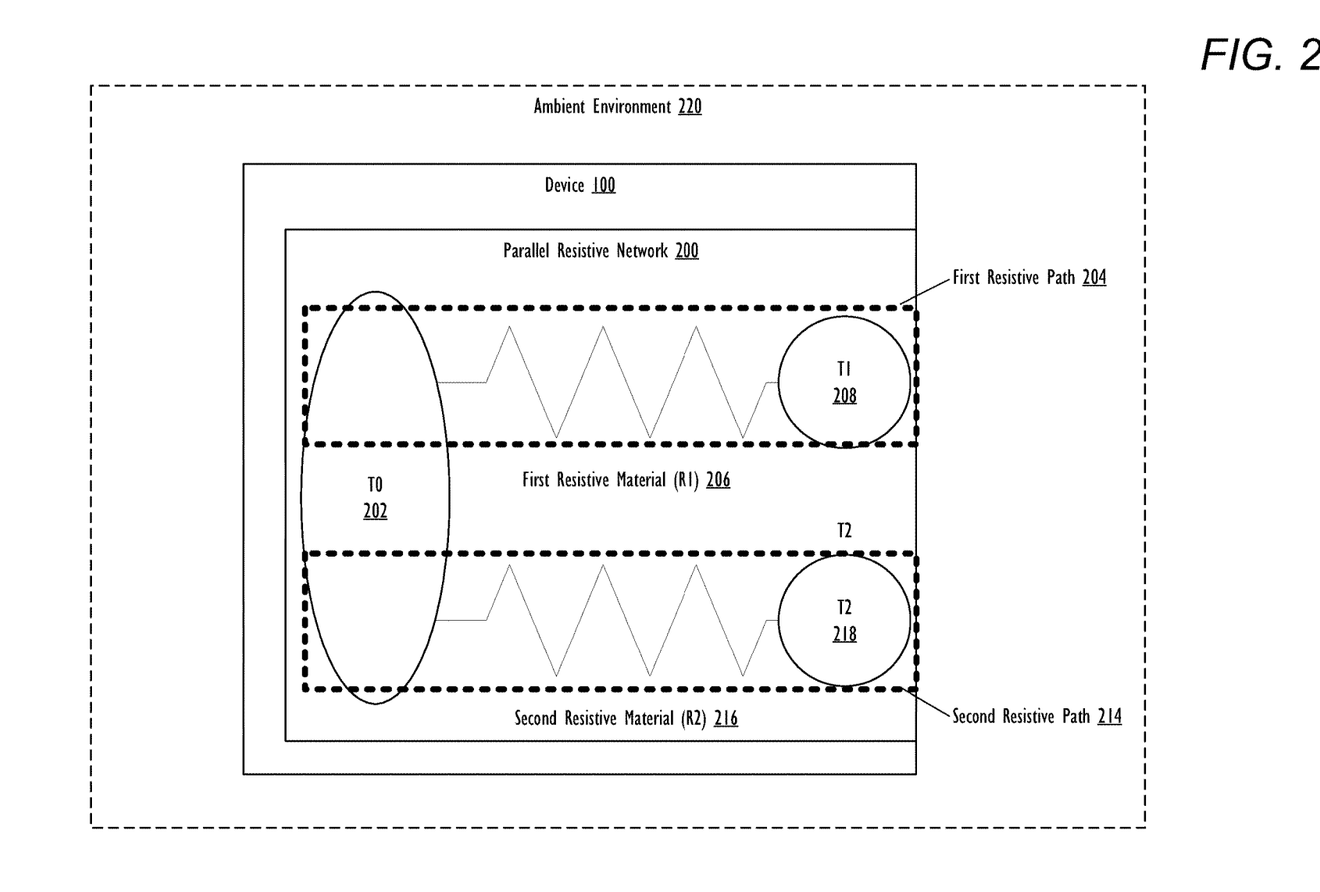
FIG. 2 illustrates an example parallel resistive network for calculating an ambient temperature and an effective heat transfer coefficient of a device, in accordance with one or more embodiments.

FIG. 2 illustrates an example parallel resistive network 200 for calculating an ambient temperature and an effective heat transfer coefficient of device 100, in accordance with one or more embodiments. Parallel resistive network 200 comprises first resistive path 204 and second resistive path 214, which is separate from first resistive path 204. First resistive path 204 and second resistive path 214 both physically extend from internal location T0 202 of device 100 to ambient environment 220. Location T0 202 is a particular location within device 100, such as a designated location on a printed circuit board. In one embodiment, location T0 202 is a location inside device 100 that is adjacent to a particular component of device 100 that generates heat, such as CPU 104. In another embodiment, location T0 202 may be a central location inside device 100.

First resistive path 204, comprises a first series path from location T0 202 to ambient environment 220. Along first resistive path 204, location T0 202 and location T1 208 are coupled via first resistive material R1 206. Second resistive path 214 comprises a second series path from location T0 202 to ambient environment 220. Along second resistive path 214, location T0 202 and location T1 208 are coupled via second resistive material R2 216. In one embodiment, one or both of T1 208 and T2 218 may be further separated from ambient environment 220 by a conductive material of device 100 that has a high conductivity and a very low electrical resistance value. As described in greater detail in FIG. 3 below, a first thermal sensor is coupled to location T0 202, a second thermal sensor is coupled to location T1 208, and a third thermal sensor is coupled to T2 218.

In one embodiment, ambient environment 220 is a gaseous environment, such as air. However, it should be noted that in one or more embodiments, device 100 may be submerged in a liquid and ambient environment 220 may be a liquid environment such as salt water, fresh water, or any other aqueous solution. In yet another embodiment, the ambient environment may include one or more objects that are heating or cooling the ambient environment (e.g., radiative body heat or a ceiling fan).

Figure 3:
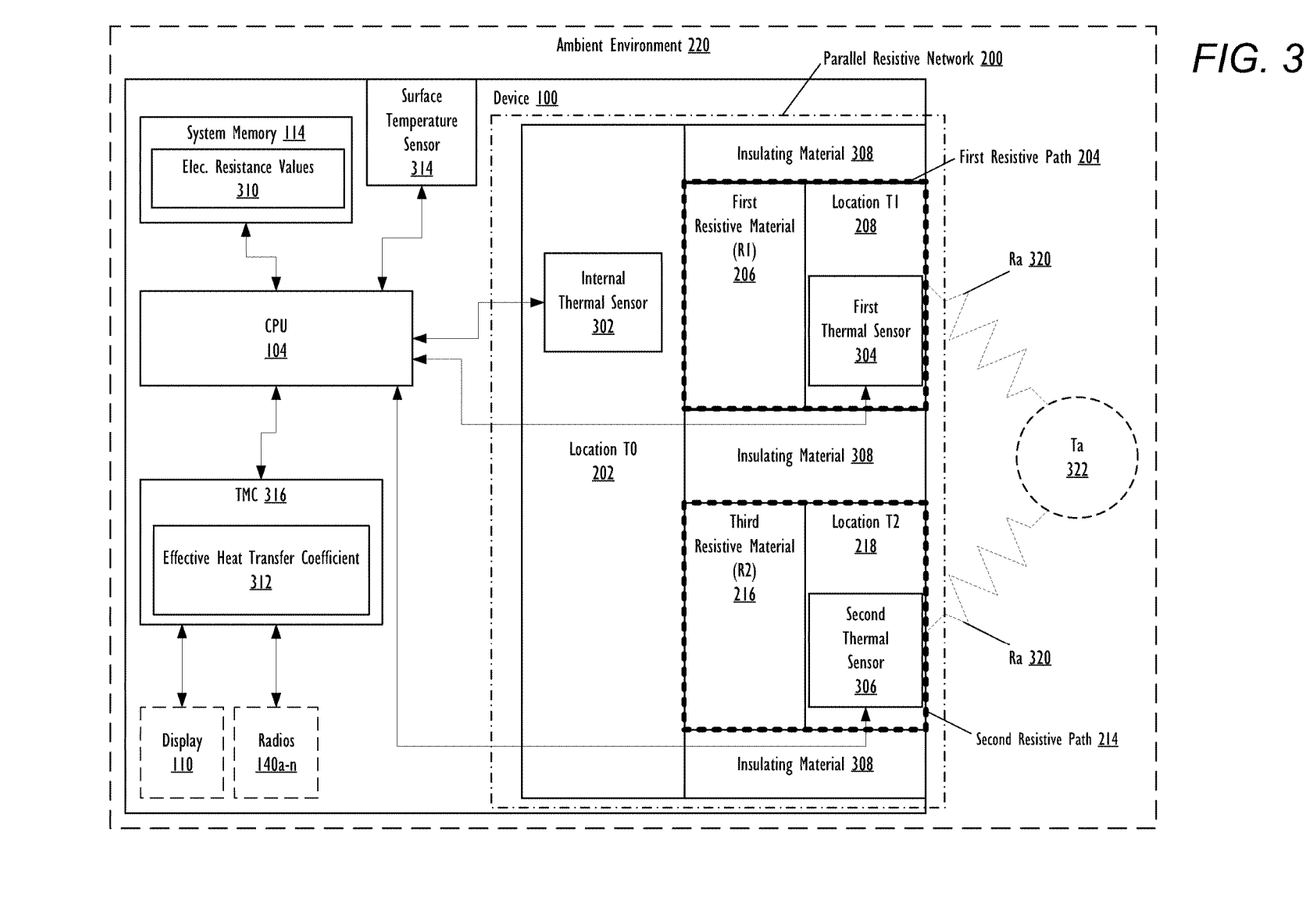
FIG. 3 illustrates a device having a parallel resistive network for calculating an ambient temperature of an environment and an effective heat transfer coefficient of the device, in accordance with one or more embodiments.

FIG. 3 illustrates device 100 having parallel resistive network 200 for calculating an effective heat transfer coefficient 312 of device 100 and an ambient temperature (Ta 322) of ambient environment 220 independent of any heat generated by device 100 to ambient environment 220, in accordance with one or more embodiments. As shown, first resistive path 204 and second resistive path 214 are separated by insulating material 308, which has a very large resistance. CPU 104 is connected to: (1) internal thermal sensor 302 at location T0 202; (2) first thermal sensor 304 at location T1 208; and (3) second thermal sensor 306 at location T2 218. It should be noted that in one or more embodiments, internal thermal sensor 302, first thermal sensor 304, and second thermal sensor 306 may be turned for a same or different temperature ranges. In one example, each of internal thermal sensor 302, first thermal sensor 304, and second thermal sensor 306 is tuned to measure temperatures in the range of 0-120° Celsius (C.). In another example, internal thermal sensor 302 is tuned to measure temperatures between the ranges of 10-100° C. and first thermal sensor 304 and second thermal sensor 306 are tuned to measure temperatures in the range of 0-50° C.

Device 100 may store, within system memory 114, electrical resistance values 310. Electrical resistance values 310 include known electrical resistance values and/or conductivity characteristics for first resistive material R1 206 and second resistive material R2 216. In another embodiment, electrical resistance values 310 may also include electrical resistance values and/or conductivity characteristics for insulating material 308 and/or any conductive material(s) that separate location T1 208 and/or T2 218 from ambient environment 220. While, electrical resistance values 310 are illustrated as being stored within system memory 114, in another embodiment, electrical resistance values 310 may be stored within another storage of device 100, such as non-volatile storage 120.

By measuring the temperatures at locations T0 202, T1 208, and T2 218 of parallel resistive network 200, device 100 may calculate, via HTU 118, the ambient temperature (Ta 322) of ambient environment 220 and effective heat transfer coefficient (1/Ra) 312 of device 100. Effective heat transfer coefficient 312 represents a rate at which heat generated by device 100 can be dissipated to ambient environment 220 in proportion to the temperature difference between the internal temperature of device 100 and Ta 322. To calculate Ta 322 and effective heat transfer coefficient 312, device 100 measures: (1) the internal temperature of device 100 at location T0 202 via internal temperatures sensor 302; (2) a first temperature at location T1 208 via first thermal sensor 304; and (3) a second temperature at location T2 218 via second thermal sensor 306. Once the temperatures at each of locations T0 202, T1 208, and T2 218 have been measured, device 100 may calculate effective heat transfer coefficient 312 and Ta 322, via HTU 118, by solving the following equations:

$$(T2-T0)/R2=(Ta-T2)/Ra$$

$$(T1-T0)/R1=(Ta-T1)/Ra$$

At the time of calculation, Ta (Ta 322) and Ra (Ra 320), which is the ambient convective resistance of ambient environment 220, are unknown. In one embodiment, HTU 118 simultaneously calculates the above system of equations using matrices. In another embodiment, the above equations may be sequentially calculated by first solving for either Ta 322 or Ra 320 in a first of the two equations and inserting the result into the second of the two equations above. By solving the equations, HTU 118 learns effective heat transfer coefficient 312 of device 100 and Ta 322 of ambient environment 220. In response to calculating effective heat transfer coefficient 312, HTU 118 provides effective heat transfer coefficient 312 and Ta 322 to TMC 316. In one embodiment, TMC 316 includes a processing device that executes TMU 116. As described in FIG. 2 above, if present, any conductive materials separating one or both of T1 208 and T2 218 from ambient environment 220 have a high conductivity and a very low electrical resistance value. Due to the high electrical conductivity and low electrical resistance of these conductive materials, the conductive materials, if present, have a negligible effect on the effective heat transfer coefficient 312 and Ta 322 and may be omitted from the above calculations.

In response to receiving effective heat transfer coefficient 312 and Ta 322, TMC 316 determines whether a current operating mode of device 100 is optimized for the ambient environment 220. As utilized herein, an operating mode refers to the configuration/operating characteristics of one or more components of device 100. For example, an operating mode may include configuration parameters for an operating frequency of CPU 104, an input/output data rate of wireless radios 140a-n, and a brightness of a backlight of display 110. An enhanced operating mode regulates the performance of one or more components of device 100 based on Ta 322 and the effective heat transfer coefficient 312. For example, an enhanced operating mode may set a maximum, minimum, or current operating frequency of CPU 104 and/or an input/output data rate of wireless radios 140a-n to a particular level. In one embodiment, the particular level is determined as a specific operating frequency and/or an input/output data rate which: (1) maximizes the performance of the device; (2) maintains a maximum surface temperature of device 100 below a pre-established maximum surface temperature threshold; and/or (3) maintains the internal temperature of device 100 below a pre-established maximum internal operating temperature threshold.

In one embodiment, for a high heat transfer coefficient 312 value (e.g., when a breeze is being applied across a surface of device 100 and/or device 100 is located in a cool ambient environment 220), the enhanced operating mode of device 100 may include an increased performance level of one or more components of device 100. In another embodiment, for a low heat transfer coefficient 312 value (e.g., the air is stagnant and/or device 100 is located in a warm ambient environment 220), the enhanced operating mode of device 100 may include a reduced performance level of one or more components of device 100. In still another embodiment, an enhanced operating mode may also maximize the configuration and/or operating characteristics of one or more components of device 100 to achieve a desired and/or optimal power consumption.

In response to determining the current operating mode of device 100 is not optimized for ambient environment 220, TMC 316 may calculate an enhanced operating mode for the device in the ambient environment. The calculated enhanced operating mode establishes at least one maximum and/or improved operating specification for at least one component of device 100 that maintains the internal temperature at location T0 202 below a pre-established maximum internal operating temperature threshold. In another embodiment, device 100 may be configured with surface temperature sensor 314 for measuring the surface temperature at an outside surface of device 100. Alternatively, in the event device 100 is not configured with surface temperature sensor 314, HTU 118 and/or TMC 316 may estimate a surface temperature of device 100 based on effective heat transfer coefficient 312, Ta 322, and the measured temperatures at T0 202, T1 208, and T2 218. In still another embodiment, the at least one maximum and/or improved operating specification for the at least one component continually maintains a maximum surface temperature of device 100 and/or an average surface temperature of device 100 below a pre-established temperature threshold.

Based on the calculated enhanced operating mode, TMC 316 may determine whether at least one modification exists that can be applied to the at least one component of device 100 that corrects for at least one of (i) the effective heat transfer coefficient 312 of the device and (ii) at least one environmental heat transfer condition in the ambient environment. The at least one modification includes at least one adjustment/change to the at least one component that modifies the current operating mode of device 100 to the enhanced operating mode. In one embodiment, the at least one modification comprises an increase or a decrease to at least one of: a brightness level of display 110, a maximum and/or current data rate of wireless radios 140a-n, and a maximum, minimum, and/or current operating frequency of CPU 104. In another embodiment, the at least one modification includes an adjustment to a pre-determined maximum internal operating temperature threshold of device 100 based on Ta 322 and effective heat transfer coefficient 312.

In response to determining at least one change exists that can be applied to the at least one component that changes the current operating mode of device 100 to the enhanced operating mode, TMC 316 may apply the at least one change to the at least one component. For example, in a cold environment, TMC 316 may increase a current operating frequency of CPU 104 to change the current operating mode of device 100 to the enhanced operating mode.

Figure 4:
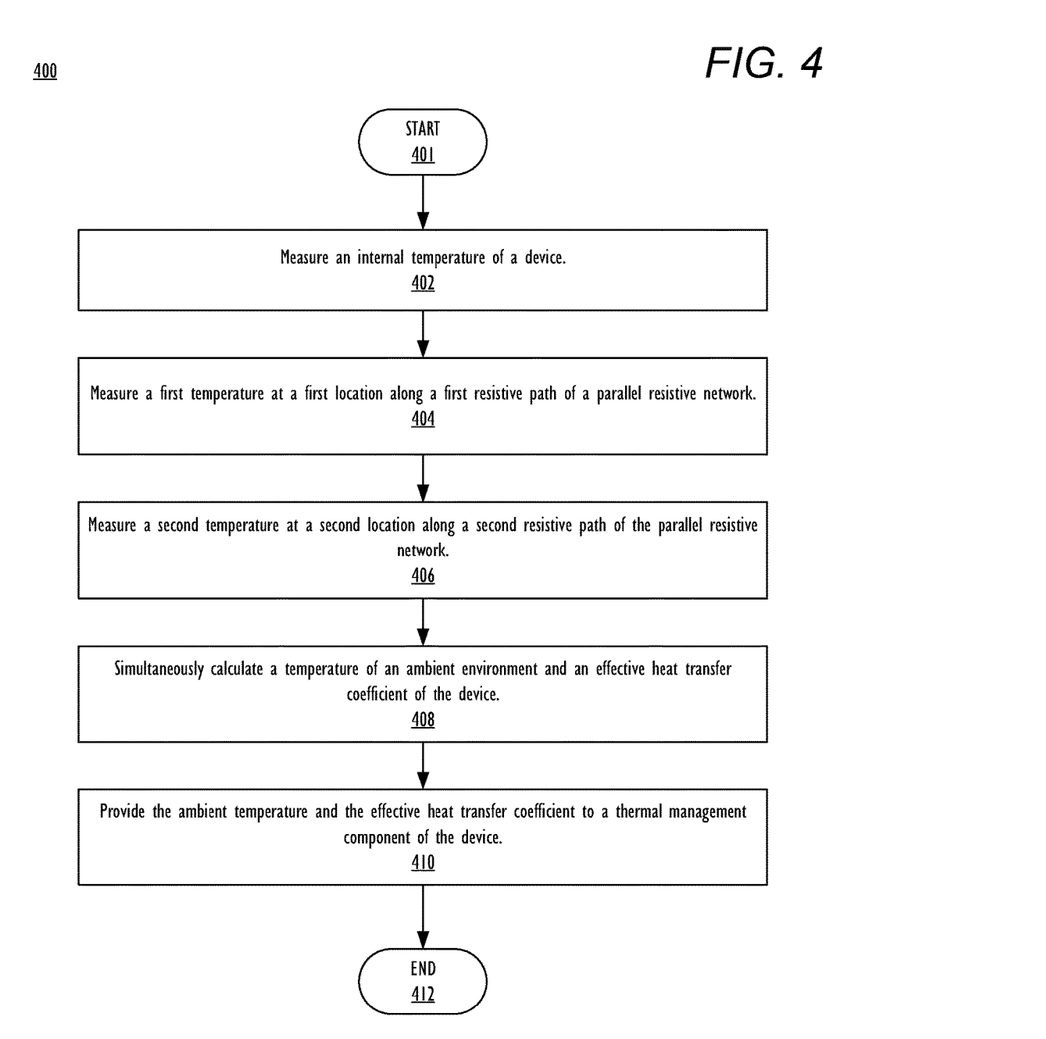
FIG. 4 is a flow chart illustrating a method for calculating an ambient temperature of an environment and an effective heat transfer coefficient of a device, in accordance with one or more embodiments.
Figure 5:
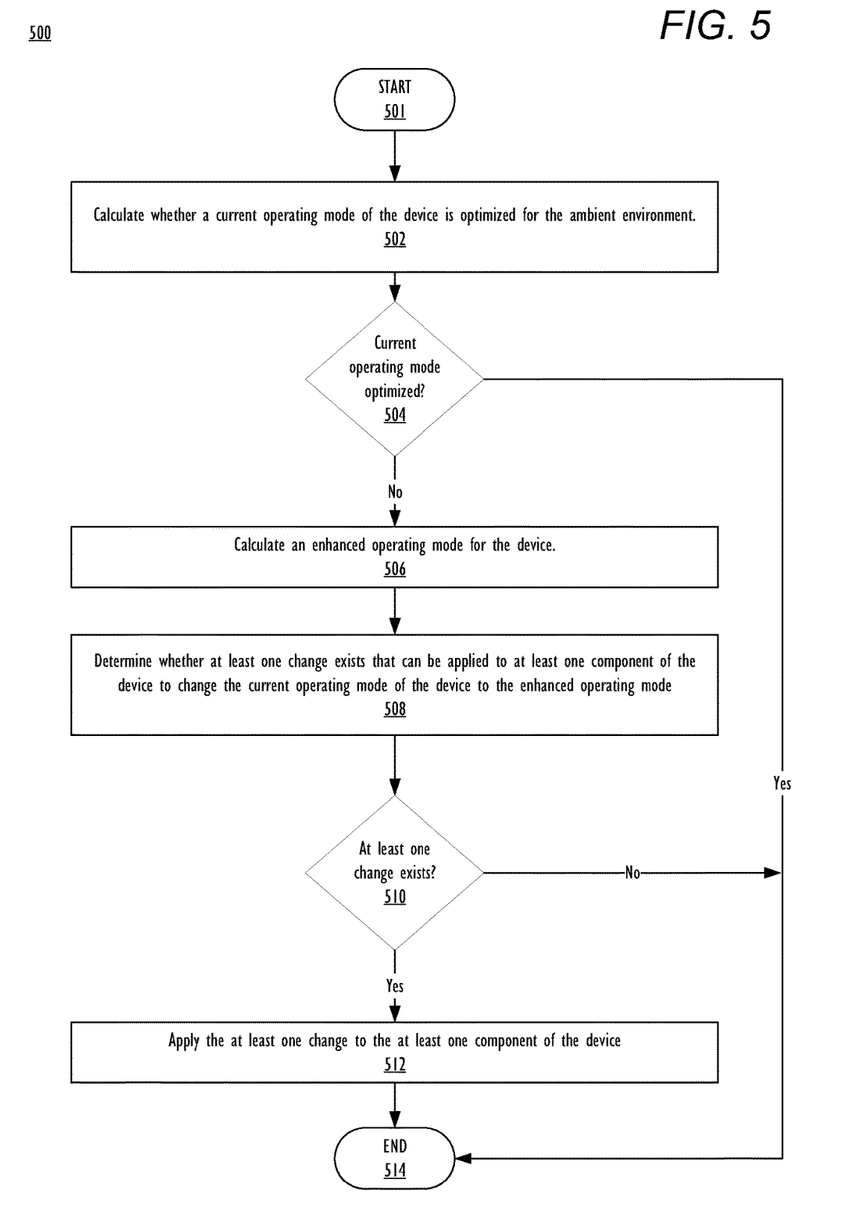
FIG. 5 is a flow chart illustrating a method for determining and applying at least one modification to a device that corrects for at least one of (i) an effective heat transfer coefficient of the device and (ii) at least one environmental heat transfer condition in the ambient environment, in accordance with one or more embodiments.

Referring now to FIGS. 4-5, there are illustrated flow charts of various methods for calculating an effective heat transfer coefficient of a device, according to one or more embodiments. Aspects of the methods are described with reference to the components of FIGS. 1-3. Several of the processes of the methods provided in FIGS. 4-5 can be implemented by CPU 104 executing software code of HTU 118 within a mobile device or generic data processing system. For simplicity, the methods described below are generally described as being performed by processor execution of HTU 118 and TMC 316 of device 100.

Referring now to FIG. 4, there is depicted a high-level flow-chart illustrating a method for calculating an effective heat transfer coefficient of a device (device 100), in accordance with one or more embodiments of the present disclosure. Method 400 commences at initiator block 401 then proceeds to block 402. At block 402, the internal temperature of device 100 is measured. The method then proceeds to block 404 where a first temperature is measured at a first location along a first resistive path of a parallel resistive network. HTU 118 then measures a second temperature at a second location along a second resistive path of the parallel resistive network (block 406). At block 408, HTU 118 calculates: (1) the ambient temperature of an ambient environment of device 100 independent of any heat generated by the device 100 to the ambient environment and (2) the effective heat transfer coefficient of device 100 based on the internal temperature, the first temperature, the second temperature, and pre-established resistive properties of the first resistive path and the second resistive path, which are located in a storage of device 100. At block 410, the effective heat transfer coefficient of device 100 and the ambient temperature of the ambient environment are provided to a thermal management component of device 100. Based on the ambient environment and the effective heat transfer coefficient, a thermal management component of device 100 may autonomously regulate the operation of a CPU and/or one or more input, output, or input/output components of device 100 in order to optimize and/or maximize the performance thereof for the rate at which heat generated by device 100 can be dissipated to the current ambient environment. The method then terminates at block 412.

Referring now to FIG. 5, there is depicted a high-level flow-chart illustrating a method for determining and applying at least one modification to a device that corrects for at least one of (i) an effective heat transfer coefficient of the device and (ii) at least one environmental heat transfer condition in the ambient environment, in accordance with one or more embodiments of the present disclosure. Method 500 commences at initiator block 501. At block 502, TMC 316 calculates whether a current operating mode of device 100 is optimized for ambient environment 220. In response to determining the current operating mode of device 100 is optimized for ambient environment 220 (block 504), method 500 terminates at block 514.

In response to determining the current operating mode of device 100 is not optimized for ambient environment 220 (block 504), TMC 316 calculates an enhanced operating mode for device 100 (block 506). TMC 316 then determines, at block 508, whether at least one change can be applied to at least one component of device 100 that will transform the current operating mode of device 100 to the enhanced operating mode. In response to determining at least one change exists (block 510), the at least one change is applied to the at least one component of device 100 (block 512). Method 500 then terminates at block 514. In response to determining no change exists that can transform the current operating mode of device 100 to the enhanced operating mode (block 510), the method 500 terminates at block 514.

In the above-described flow charts, one or more of the method processes may be embodied in a computer readable device containing computer readable code such that a series of steps are performed when the computer readable code is executed on a computing device. In some implementations, certain steps of the methods are combined, performed simultaneously or in a different order, or perhaps omitted, without deviating from the scope of the disclosure. Thus, while the method steps are described and illustrated in a particular sequence, use of a specific sequence of steps is not meant to imply any limitations on the disclosure. Changes may be made with regards to the sequence of steps without departing from the spirit or scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object oriented programming language, without limitation. These computer program instructions may be provided to a processor of a general purpose computer, special purpose computer, or other programmable data processing apparatus to produce a machine that performs the method for implementing the functions/acts specified in the flowchart and/or block diagram block or blocks. The methods are implemented when the instructions are executed via the processor of the computer or other programmable data processing apparatus.

As will be further appreciated, the processes in embodiments of the present disclosure may be implemented using any combination of software, firmware, or hardware. Accordingly, aspects of the present disclosure may take the form of an entirely hardware embodiment or an embodiment combining software (including firmware, resident software, micro-code, etc.) and hardware aspects that may all generally be referred to herein as a "circuit," "module," or "system." Furthermore, aspects of the present disclosure may take the form of a computer program product embodied in one or more computer readable storage device(s) having computer readable program code embodied thereon. Any combination of one or more computer readable storage device(s) may be utilized. The computer readable storage device may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage device would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage device may be any tangible medium that can contain, or store a program for use by or in connection with an instruction execution system, apparatus, or device.

While the disclosure has been described with reference to example embodiments, it will be understood by those skilled in the art that various changes may be made and equivalents may be substituted for elements thereof without departing from the scope of the disclosure. In addition, many modifications may be made to adapt a particular system, device, or component thereof to the teachings of the disclosure without departing from the scope thereof. Therefore, it is intended that the disclosure not be limited to the particular embodiments disclosed for carrying out this disclosure, but that the disclosure will include all embodiments falling within the scope of the appended claims.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method comprising:
   measuring an internal temperature at a particular location within a device;
   measuring, via a first thermal sensor, a first temperature at a first location along a first resistive path of a parallel resistive network having a pair of resistive paths, wherein the first resistive path physically extends between the particular location and an ambient environment, the first resistive path having first pre-established resistive properties;
   measuring, via a second thermal sensor, a second temperature at a second location along a second resistive path of the parallel resistive network, wherein the second resistive path physically extends between the particular location and the ambient environment, wherein the second resistive path is parallel to the first resistive path, the second resistive path having second pre-established resistive properties;
   simultaneously calculating, based on the internal temperature, the first temperature, the second temperature, the first pre-established resistive properties, and the second pre-established resistive properties: an ambient temperature of the ambient environment and an effective heat transfer coefficient of the device, wherein the effective heat transfer coefficient represents a rate at which heat generated by the device can be dissipated to the ambient environment in proportion to the temperature difference between the device and the ambient temperature; and
   providing the ambient temperature and the effective heat transfer coefficient to a thermal management component of the device.

2. The method of claim 1, wherein:
   the internal temperature at the particular location is measured using an internal thermal sensor;
   the particular location and the first thermal sensor are separated by a first resistive material, and the first thermal sensor;
   the particular location and the second thermal sensor are separated by a second resistive material that is different from the first resistive material;
   the first pre-established resistive properties are different from the second pre-established resistive properties;
   the first pre-established resistive properties include a resistance of the first resistive material; and
   the second pre-established resistive properties include a resistance of the second resistive material.

3. The method of claim 2, wherein each of the internal thermal sensor, the first thermal sensor, and the second thermal sensor is tuned for a temperature range, and wherein any one thermal sensor of the internal thermal sensor, the first thermal sensor, and the second thermal sensor can be tuned for a particular temperature range that corresponds to only that thermal sensor.

4. The method of claim 1, further comprising:
   determining, based on the ambient temperature of the ambient environment and the effective heat transfer coefficient of the device, whether a current operating mode of the device is optimized for the ambient environment; and
   in response to determining that the current operating mode of the device is not optimized for the ambient environment, applying at least one modification to the device that corrects for at least one of (i) the effective heat transfer coefficient of the device and (ii) at least one environmental heat transfer condition in the ambient environment.

5. The method of claim 4, wherein the at least one modification comprises a change from among an increase to and a decrease to at least one of: a brightness level of a display, a maximum data rate of at least one wireless radio, and an operating frequency of a processor of the device.

6. The method of claim 4, wherein applying the at least one modification to the device further comprises:
   calculating an enhanced operating mode for the device, wherein the enhanced operating mode establishes, for the ambient environment, at least one maximum operating specification for at least one component of the device that maintains a surface temperature of the device below a pre-established maximum surface temperature threshold and maintains the internal temperature below a pre-established maximum internal operating temperature threshold;
   determining, based on the calculated enhanced operating mode, whether at least one change exists that can be applied to the at least one component that changes a current operating mode of the device to the enhanced operating mode, wherein the at least one modification includes the at least one change, and wherein the at least one change indicates that the current operating mode is not optimized for the ambient environment; and
   in response to determining at least one change exists that can be applied to the at least one component that changes the current operating mode of the device to the enhanced operating mode, applying the at least one change to the at least one component.

7. The method of claim 4, further comprising:
   adjusting a pre-determined maximum internal operating temperature threshold of the device based on the ambient temperature of the ambient environment and the effective heat transfer coefficient.

8. The method of claim 1, wherein the first resistive path and the second resistive path are separated by an insulating material.

9. A device comprising:
   a thermal management component;
   an internal thermal sensor at a particular location within the device and which measures an internal temperature of the device;
   a parallel resistive network that includes:
      a first resistive path extending between the particular location and an ambient environment of the device and comprising a first thermal sensor, the first resistive path having first pre-established resistive properties; and
      a second resistive path extending in parallel to the first resistive path between the particular location and the ambient environment and comprising a second thermal sensor, the second resistive path having second pre-established resistive properties; and
   a processor communicatively coupled to the internal thermal sensor, the first thermal sensor, and the second thermal sensor and which receives a signal from the internal thermal sensor that identifies an internal temperature of the device at the particular location, the processor executing a thermal response firmware, wherein:
      the processor receives, from the first thermal sensor, a first temperature at a first location along the first resistive path;

the processor receives, from the second thermal sensor, a second temperature at a second location along the second resistive path;

the processor simultaneously calculates, based on the internal temperature, the first temperature, the second temperature, the first pre-established resistive properties, and the second pre-established resistive properties; an ambient temperature of the ambient environment and an effective heat transfer coefficient of the device, wherein the effective heat transfer coefficient represents a rate at which heat generated by the device can be dissipated to the ambient environment in proportion to the temperature difference between the device and the ambient temperature; and the processor provides the ambient temperature and the effective heat transfer coefficient to the thermal management component to implement thermal management on the device.

10. The device of claim 9, wherein:

the particular location and the first thermal sensor are separated by a first resistive material;

the particular location and the second thermal sensor are separated by a second resistive material that is different from the first resistive material;

the first pre-established resistive properties are different from the second pre-established resistive properties;

the first pre-established resistive properties include a resistance of the first resistive material; and the second pre-established resistive properties include a resistance of the second resistive material.

11. The device of claim 10, wherein each of the internal thermal sensor, the first thermal sensor, and the second thermal sensor is tuned for a temperature range, and wherein any one thermal sensor of the internal thermal sensor, the first thermal sensor, and the second thermal sensor can be tuned for a particular temperature range that corresponds to only that thermal sensor.

12. The device of claim 10, further comprising, in response to receiving the effective heat transfer coefficient:

the thermal management component determines, based on the ambient temperature of the ambient environment and the effective heat transfer coefficient of the device, whether a current operating mode of the device is optimized for the ambient environment; and in response to determining that the current operating mode of the device is not optimized for the ambient environment, the thermal management component applies at least one modification to the device that corrects for at least one of (i) the effective heat transfer coefficient of the device and (ii) at least one environmental heat transfer condition in the ambient environment.

13. The device of claim 12, wherein the at least one modification comprises a change from among an increase to and a decrease to at least one of: a brightness level of a display, a maximum data rate of at least one wireless radio of the device, and an operating frequency of the processor.

14. The device of claim 12, wherein in determining whether a current operating mode of the device is optimized for the ambient environment:

the thermal management component calculates an enhanced operating mode for the device, wherein the enhanced operating mode establishes, for the ambient environment, at least one maximum operating specification for at least one component of the device that maintains a surface temperature of the device below a pre-established maximum surface temperature threshold and maintains the internal temperature below a pre-established maximum internal operating temperature threshold;

the thermal management component determines, based on the enhanced operating mode, whether at least one change exists that can be applied to the at least one component that changes a current operating mode of the device to the enhanced operating mode, wherein the at least one modification includes the at least one change, and wherein the at least one change indicates that the current operating mode is not optimized for the ambient environment; and in response to determining at least one change exists that can be applied to the at least one component that changes the current operating mode of the device to the enhanced operating mode, the thermal management component applies the at least one change to the one component.

15. The device of claim 12, wherein:

the thermal management component adjusts a pre-determined maximum internal operating temperature threshold of the device based on the ambient temperature of the ambient environment and the effective heat transfer coefficient.

16. A computer program product comprising:

a computer readable storage device; and program code on the computer readable storage device that when executed within a processor associated with a device, the program code enables the device to provide the functionality of:

receiving an input of an internal temperature measured at a particular location within the device;

receiving a first temperature measured at a first location along a first resistive path of a parallel resistive network having a pair of resistive paths, the first resistive path having first pre-established resistive properties, wherein the first resistive path physically extends between the particular location and an ambient environment;

receiving a second temperature measured at a second location along a second resistive path of the parallel resistive network, wherein the second resistive path physically extends between the particular location and the ambient environment, the second resistive path having second pre-established resistive properties, and wherein the second resistive path is parallel to the first resistive path;

simultaneously calculating, based on the internal temperature, the first temperature, the second temperature, and pre-established resistive properties of the first resistive path and the second resistive path, an ambient temperature of the ambient environment and an effective heat transfer coefficient of the device, wherein the effective heat transfer coefficient represents a rate at which heat generated by the device can be dissipated to the ambient environment in proportion to the temperature difference between the device and the ambient temperature; and providing the ambient temperature and the effective heat transfer coefficient to a thermal management component of the device.

17. The computer program product of claim 16, wherein:

the internal temperature at the particular location is measured using an internal thermal sensor of the device;

the first temperature at the first location is measured using a first thermal sensor;

the particular location and the first thermal sensor are separated by a first resistive material;

the second temperature at the second location is measured using a second thermal sensor;

the particular location and the second thermal sensor are separated by a second resistive material that is different from the first resistive material;

the first pre-established resistive properties are different from the second pre-established resistive properties;

the first pre-established resistive properties include a resistance of the first resistive material; and the second pre-established resistive properties include a resistance of the second resistive material.

18. The computer program product of claim 17, wherein the program code further comprising code that enables the device to provide the functionality of:

determining, based on the ambient temperature of the ambient environment and the effective heat transfer coefficient of the device, whether a current operating mode of the device is optimized for the ambient environment; and in response to determining that the current operating mode of the device is not optimized for the ambient environment, applying at least one modification to the device that corrects for at least one of (i) the effective heat transfer coefficient of the device and (ii) at least one environmental heat transfer condition in the ambient environment.

19. The computer program product of claim 18, wherein the program code for determining whether a current operating mode of the device is optimized for the ambient environment further comprises code that enables the device to provide the functionality of:

calculating an enhanced operating mode for the device, wherein the enhanced operating mode establishes, for the ambient environment, at least one maximum operating specification for at least one component of the device that maintains a surface temperature of the device below a pre-established surface temperature threshold and maintains the internal temperature below a pre-established maximum internal operating temperature threshold;

determining, based on the calculated enhanced operating mode, whether at least one change exists that can be applied to the at least one component that changes a current operating mode of the device to the enhanced operating mode, wherein the at least one modification includes the at least one change, and wherein the at least one change indicates that the current operating mode is not optimized for the ambient environment; and in response to determining at least one change exists that can be applied to the at least one component that changes the current operating mode of the device to the enhanced operating mode, applying the at least one change to the at least one component.

* * * * *